United States Patent [19]

Larsen

[11] Patent Number: 5,637,584
[45] Date of Patent: Jun. 10, 1997

[54] SOLVATE OF OLANZAPINE

[75] Inventor: Samuel D. Larsen, West Lafayette, Ind.

[73] Assignees: Eli Lilly and Company, Indianapolis, Ind.; Lilly Industries Limited, Hampshire, England

[21] Appl. No.: 410,263

[22] Filed: Mar. 24, 1995

[51] Int. Cl.[6] .................. A61K 31/55; C07D 495/04; C07D 243/10
[52] U.S. Cl. ............................. 514/220; 540/557
[58] Field of Search ................ 540/557; 514/220

[56] References Cited

U.S. PATENT DOCUMENTS

| 3,951,981 | 4/1976 | Safir et al. ............................ 260/268 |
| 4,115,568 | 9/1978 | Chakrabarti et al. .................. 424/250 |
| 4,337,198 | 6/1982 | Sorg et al. ........................... 260/243.3 |
| 4,542,131 | 9/1985 | Chakrabarti et al. .................. 514/220 |
| 5,229,382 | 7/1993 | Chakrabarti et al. .................. 514/220 |
| 5,457,101 | 10/1995 | Greenwood et al. .................. 514/220 |
| 5,561,127 | 10/1995 | Tehim et al. .......................... 514/211 |

*Primary Examiner*—Joseph McKane
*Assistant Examiner*—Richard S. Myers, Jr.
*Attorney, Agent, or Firm*—MaCharri Vorndran-Jones; David E. Boone

[57] ABSTRACT

The invention provides a methylene chloride solvate of 2-methyl-4-(4-methyl-1-piperazinyl)-10H-thieno[2,3-b][1,5]benzodiazepine. The invention provides a method for using such solvate.

2 Claims, No Drawings

SOLVATE OF OLANZAPINE

FIELD OF THE INVENTION

This invention relates to a methylene chloride solvate of 2-methyl-4-(4-methyl-1-piperazinyl)-10H-thieno[2,3-b][1,5]benzodiazepine and a process for using such methylene chloride solvate.

BACKGROUND OF THE INVENTION

Anhydrous Form I olanzapine compound has useful central nervous system activity.

Applicants have discovered that 2-methyl-4-(4-methyl-1-piperazinyl)-10H-thieno[2,3-b][1,5]benzodiazepine (olanzapine) exists in two anhydrous forms which are clearly distinguishable by X-ray powder diffractometry. Unfortunately, anhydrous Form II 2-methyl-4-(4-methyl-1-piperazinyl)-10H-thieno[2,3-b][1,5]benzodiazepine is metastable and is therefore not well suited for commercial use in pharmaceutical formulations. However, surprisingly and in accordance with the invention, it has now been discovered that the second polymorph of 2-methyl-4-(4-methyl-1-piperazinyl)-10H-thieno[2,3-b][1,5]benzodiazepine, designated as anhydrous Form I olanzapine, is stable and is therefore well adapted for commercial use in pharmaceutical formulations.

It is desirable to prepare the substantially pure anhydrous Form I crystalline olanzapine to assure uniformity of product. Anhydrous Form I 2-methyl-4-(4-methyl-1-piperazinyl)-10H-thieno[2,3-b][1,5]benzodiazepine can be prepared via a convenient, efficient, and ecologically acceptable process which utilizes the methylene chloride solvate of olanzapine claimed herein.

The crystalline anhydrous Form I 2-methyl-4-(4-methyl-1-piperazinyl)-10H-thieno[2,3-b][1,5]benzodiazepine (Form I) and process for preparing Form I are particularly important for the commercial development of the pharmaceutically active anhydrous Form I olanzapine.

The present invention provides the desired methylene chloride solvate of olanzapine which is useful for preparing the desired anhydrous Form I 2-methyl-4-(4-methyl-1-piperazinyl)-10H-thieno[2,3-b][1,5]benzodiazepine.

SUMMARY OF THE INVENTION

The present invention provides a methylene chloride crystalline solvate of 2-methyl-4-(4-methyl-1-piperazinyl)-10H-thieno[2,3-b][1,5]benzodiazepine (olanzapine).

The present invention provides a process for preparing anhydrous Form I using a methylene chloride solvate comprising drying such methylene chloride solvate and crystallizing the dried material in a solvent selected from the group consisting of aromatic hydrocarbons, $C_3$–$C_9$ ketones, $C_3$–$C_9$ branched alcohols, $C_3$–$C_9$ esters, $C_5$–$C_9$ hydrocarbons, $C_3$–$C_9$ ethers, and cyclic ethers in the presence of Form I 2-methyl-4-(4-methyl-1-piperazinyl)-10H-thieno[2,3b][1,5]benzodiazepine.

DETAILED DESCRIPTION OF THE INVENTION

Applicants have discovered that 2-methyl-4-(4-methyl-1-piperazinyl)-10H-thieno[2,3-b][1,5]benzodiazepine, which is a compound of Formula(I):

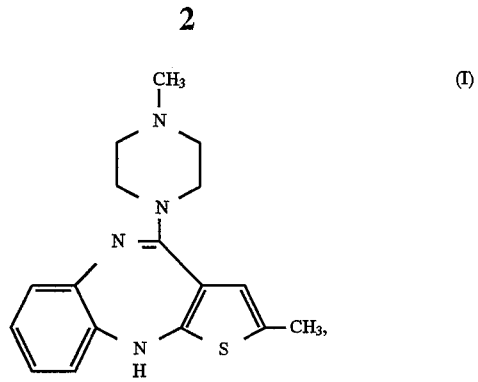

exists as two different anhydrous forms which are distinguishable by x-ray powder diffractometry. As discussed supra., the two anhydrous forms have been designated Form I and Form II. For stable commercial pharmaceutical preparations, purified anhydrous Form I 2-methyl-4-(4-methyl-1-piperazinyl)-10H-thieno[2,3-b][1,5]benzodiazepine (Form I) must be substantially free from Form II impurity in order to comply with regulatory requirements.

The x-ray powder diffraction patterns set forth herein were obtained with a copper $K_\alpha$ of wavelength $\lambda = 1.541$ Å. The interplanar spacings are in the column marked "d" are in Angstroms. The typical relative intensities are in the column marked "$I/I_1$".

As used herein, the crystallization solvent used to prepare substantially pure Form I is one or more selected from the group consisting of aromatic hydrocarbons, $C_3$–$C_9$ ketones, $C_3$–$C_9$ branched alcohols, $C_3$–$C_9$ esters, $C_5$–$C_9$ hydrocarbons, $C_3$–$C_9$ ethers, and cyclic ethers. The term "aromatic hydrocarbon" refers to a $C_4$–$C_6$ alkyl aromatic solvent which may include substituted aromatics. Examples of aromatic hydrocarbons include, but are not limited to toluene, benzene, and the like. The term "$C_5$–$C_9$ hydrocarbons" refer to $C_5$–$C_9$ alkyl solvents which may be substituted, branched or unbranched alkyl. Such hydrocarbon solvents include, but are not limited to straight or branched heptane, octane, pentane, and the like.

The term "$C_3$–$C_9$ esters" refers to straight or branched esters which may optionally be substituted.

The term "$C_3$–$C_9$ ketones" refers to straight or branched ketones which may optionally be substituted. The term "ethers" refer to lower alkyl ($C_2$–$C_8$) alkyl ethers which may be straight, branched or substituted. The term ether shall include but is not limited to, for example, t-butyl methylether, and the like.

The term "cyclic ether" shall refer to a $C_5$–$C_7$ cyclic ether which may be optionally substituted. It is especially preferred that the ether solvent is dry. It is particularly preferred that such dry ether shall contain less than about 1% water.

As used herein, the term "substituted" shall refer to from about one to about three non-hydrocarbon substituents which may be selected from the group consisting, for example, of $CF_3$, Cl, Br, F, I, and the like. When the solvent includes a Cl substituent, then the solvent molecule shall additionally include at least two carbon atoms. The suggested substituents are in no way exhaustive. Applicants envision that other non-hydrocarbon substituents will provide solvents having the desired characteristics.

Especially preferred solvents for the crystallization process are one or more selected from the group consisting of ethyl acetate, acetone, 2-propanol, tetrahydrofuran, and toluene.

As used herein "substantially pure" shall refer to anhydrous Form I associated with about <5% undesired polymorph; and most preferably it shall refer to about <2% Form II. It is further preferred that "substantially pure" shall refer to <0.5% related substances. When the Form I polymorph is formulated as a pharmaceutical composition, "substantially pure" shall preferably refer to about <15% undesired polymorph; more preferably, the term shall refer to about <10% undesired polymorph when the Form I polymorph is formulated as a pharmaceutical, and it is especially preferred that the term shall refer to about <5% Form II polymorph when the substantially pure substance is formulated.

As used herein, the term "2-methyl-4-(4-methyl-1-piperazinyl)-10H-thieno[2,3-b][1,5]benzodiazepine" refers to a technical grade of 2-methyl-4-(4-methyl-1-piperazinyl)-10H-thieno[2,3-b][1,5]benzodiazepine when no specific solvate or polymorph is named. Typically, the technical grade olanzapine contains less than about 5% undesired related substances and may be a mixed polymorph. Such technical grade olanzapine may contain less than about 1% undesired related substances.

The term "crude" refers to a form of olanzapine typically associated with undesired polymorph and/or greater than about 5% undesired related substances. Such crude grade olanzapine may contain less than about 1% undesired related substances.

The term "in the presence of Form I" means that one or more substantially pure Form I olanzapine crystals are present. Most preferably, there are sufficient crystals to provide a seeding effect, such that substantially all of the anhydrous polymorph so prepared is the desired Form I olanzapine polymorph.

The x-ray powder diffraction patterns set forth herein were obtained with a copper $K_\alpha$ of wavelength $\lambda=1.541$ Å. The interplanar spacings are in the column marked "d" are in Angstroms. The typical relative intensities are in the column marked "$I/I_1$".

Anhydrous Form I olanzapine has a typical X-ray powder diffraction pattern substantially as follows, using an Siemans D5000 X-ray powder diffractometer, wherein d represents the interplaner spacing:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

Anhydrous Form II olanzapine (Form II) has a typical X-ray powder diffraction pattern substantially as follows, using an Siemans D5000 X-ray powder diffractometer, wherein d represents the interplaner spacing:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "solvate" shall refer to a true solvate of olanzapine, wherein the solvent molecule is held within the crystalline latice.

A preferred embodiment of the invention is the crystalline mono(methylene chloride) solvate of 2-methyl-4-(4-methyl-1-piperazinyl)-10H-thieno[2,3-b][1,5]benzodiazepine exhibiting substantially the x-ray powder diffraction pattern of Table 1, using an Enraf-Nonius CAD4 kappa axis diffractometer:

TABLE 1

| Mono(methylene chloride) Solvate | |
|---|---|
| d | $I/I_0$ |
| 10.3721 | 67.90 |
| 9.4579 | 26.59 |
| 8.0541 | 4.90 |
| 7.4887 | 10.55 |

TABLE 1-continued

Mono(methylene chloride) Solvate

| d | $I/I_0$ |
|---|---|
| 6.7033 | 3.39 |
| 6.5341 | 3.22 |
| 5.6880 | 3.15 |
| 5.5067 | 3.72 |
| 5.2097 | 100.00 |
| 4.7905 | 3.41 |
| 4.5342 | 7.43 |
| 4.3932 | 18.60 |
| 4.1624 | 4.31 |
| 4.0157 | 8.73 |
| 3.9705 | 23.40 |
| 3.8522 | 2.60 |
| 3.7535 | 20.98 |
| 3.6804 | 8.75 |
| 3.6335 | 3.06 |
| 3.5198 | 5.90 |
| 3.4689 | 4.48 |
| 3.4399 | 3.00 |
| 3.3491 | 8.78 |
| 3.2431 | 2.27 |
| 3.1714 | 6.49 |
| 3.1075 | 2.54 |
| 3.0437 | 3.65 |
| 2.9476 | 5.31 |
| 2.8872 | 3.19 |
| 2.8466 | 2.18 |
| 2.7906 | 2.42 |
| 2.7239 | 5.74 |
| 2.6859 | 6.21 |
| 2.6116 | 7.11 |
| 2.5728 | 3.36 |

The x-ray powder diffraction pattern in Table I was obtained with a copper $K_\alpha$ of wavelength $\lambda=1.54184$ Å. The interplanar spacings are in the column marked "d" are in Angstroms. The typical relative intensities are in the column marked "$I/I_1$".

Especially preferred solvents for the crystallization process are one or more selected from the group consisting of ethyl acetate, acetone, 2-propanol, tetrahydrofuran, and toluene.

The compounds and processes of the present invention are useful for preparing compounds having beneficial central nervous system activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of this invention include the following:

A) A mono (methylene chloride) solvate of 2-methyl-4-(4-methyl-1-piperazinyl)-10H-thieno[2,3-b][1,5]benzodiazepine B) Substantially pure refers to ≦5% undesired polymorph;

C) Substantially pure refers to ≦2% undesired polymorph;

The Form I olanzapine prepared by the process of this invention has useful central nervous system activity. This activity has been demonstrated using well-established procedures. For example, the anhydrous Form I compound has been assessed in a number of standard behavior tests predictive of antipsychotic activity. The claimed compound antagonised apomorphine-induced climbing behavior and hypothermia in mice. See Moore, N. A. et al *Psychopharmacology* 94 (2), 263–266 (1988). The compound also inhibits conditioned avoidance response in rats, but unlike standard antipsychotic compounds, the compound of this invention induces cataleptsy only at higher doses. This separation between the doses required to block conditioned avoidance response and to induce catalepsy indicates that the compound is less likely to induce extrapyramidal side effects in the clinic.

In addition, anhyrous Form I olanzapine has been found to have a favorable profile of activity in a number of in vitro binding assays, designed to measure the degree of binding to neural receptors. For example, the compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman et al Nature 216:717 (1976)) binding assays respectively.

Further, the compound is active at the 5-HT-2 receptor and 5-HT1C receptor. The in vitro results would indicate that the compound is effective in the treatment of psychotic conditions but less likely to induce extra pyramidal side-effects.

As used herein the term "psychosis" shall mean pathologic psychological conditions which are psychoses or may be associated with psychotic features including, but not limited to the following disorders which have been characterized in the DSM-III-R. *Diagnostic and Statistical Manual of Mental Disorders, Revised,* 3rd Ed. (1980). The DSM-III-R was prepared by the Task Force on Nomenclature and Statistics of the American Psychiatric Association, and provides clear descriptions of diagnostic catagories. The numbers in parenthesis refer to the DSM-III-R categories. The skilled artisan will recognize that there are alternative nomenclatures, nosologies, and classification systems for pathologic psychological conditions and that these systems evolve with medical scientific progress.

Examples of pathologic psychologic conditions which may be treated using anhydrous Form I 2-methyl-4-(4-methyl-1-piperazinyl)-10H-thieno[2,3-b][1,5]benzodiazepine include, but are not limited to, Conduct Disorder, Group Type (312.20), Conduct Disorder, Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Multi-infarct dementia, with Delirium (290.41), Multi-infarct dementia, with Delusions (290.42), Multi-infarct dementia, with Depression (290.43), Multi-infarct dementia, Uncomplicated (290.40), Senile Dementia NOS (290.00), Presenile Dementia NOS (290.10), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delirium (292.81), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP) or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Mood Disorder (292.84), Phencyclidine (PCP) or Similarly Acting Arylcyclohexylamine Organic Mental Disorder NOS (292.90), Other or Unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive Substance Hallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.82), Organic Mood Disorder (293.83), Organic Anxiety Disorder (294.80), Organic Mental Disorder (294.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39).

Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Subchronic (295.11), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic (295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, Unspecified (295.60), Delusional (Paranoid) Disorder (297.10), Brief Reactive Psychosis (298.80), Schizophreniform Disorder (295.40), Schizoaffective Disorder (295.70), Induced Psychotic Disorder (297.30), Psychotic Disorder NOS (Atypical Psychosis) (298.90), Bipolar Disorder, Mixed, Severe, without Psychotic Features 296.63), Bipolar Disorder, Manic, Severe, without Psychotic Features (296.43), Bipolar Disorder, Depressed, Severe, without Psychotic Features (296.53), Major Depression, Single Episode, Severe, without Psychotic Features (296.23), Major Depression, Recurrent, Severe, without Psychotic Features (296.33), Bipolar Disorder, Mixed, with Psychotic Features (296.64), Bipolar Disorder, Manic, with Psychotic Features (296.44), Bipolar Disorder, Depressed, with Psychotic Features (296.54), Bipolar Disorder NOS (296.70), Major Depression, Single Episode, with Psychotic Features (296.24), and Major Depression, Recurrent with Psychotic Features (296.34).

Preferably, an effective amount of anhydrous Form I 2-methyl-4-(4-methyl-1-piperazinyl)-10H-thieno-[2,3-b][1,5]benzodiazepine, or an acid addition salt thereof, is used for the treatment of Tourette's Disorder; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, with Psychotic Features; Hebephrenic Schizophrenia; Post-Schizophrenic Depression; Delusional Disorder; and Other Persistent Delusional Disorders.

More preferredly, anhydrous Form I 2-methyl-4(4-methyl-1-piperazinyl)-10H-thieno-[2,3-b][1,5]benzodiazepine is used to treat the following pathologic psychological conditions including Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis);Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, with Psychotic Features; Hebephrenic Schizophrenia; Post-Schizophrenic Depression; Delusional Disorder; and Other Persistent Delusional Disorders.

Examples of conditions which are most preferredly treated using anhydrous Form I 2-methyl-4-(4-methyl-1-piperazinyl)-10H-thieno-[2,3-b][1,5]benzodiazepine include Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; and Hebephrenic Schizophrenia.

Examples of anxiety disorders which may more preferredly be treated using an effective amount of anhydrous Form I 2-methyl-4-(4-methyl-1-piperazinyl)-10H-thieno[2,3-b][1,5]benzodiazepine, or an acid addition salt thereof, include Psychoactive Substance Anxiety Disorder; Organic Anxiety Disorder; Obsessive Compulsive Disorder; Post-traumatic Stress Disorder; Generalized Anxiety Disorder; and Anxiety Disorder NOS.

Examples of the anxiety disorders which are most preferredly treated using anhydrous Form I 2-methyl-4-(4-methyl-1-piperazinyl)-10H-thieno-[2,3-b][1,5] benzodiazepine include Organic Anxiety Disorder; Obsessive Compulsive Disorder; Post-traumatic Stress Disorder; Generalized Anxiety Disorder; and Anxiety Disorder NOS.

As used herein the term "Functional Bowel Disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "Functional Bowel Disorder" includes but is not limited to irritable bowel syndrome, hypermotility, ichlasia, hypertonic lower esophogeal sphincter, tachygastria, constipation, hypermotility associated with irritable bowel syndrome.

Functional Bowel Disorders are characterized by abnormal bowel function without detectable structural abnormalities. Abnormal bowel function includes diarrhea, constipation, mucorrhea, and pain or discomfort over the course of the sigmoid colon. Such disorders are influenced by psychological factors and stressful life situations.

The Functional Bowel Disorder, Irritable Bowel Syndrome (IBS), is one of the most commonly encountered gastrointestinal disorders. Between 20% and 50% of patients referred to gastrointestinal clinics suffer from IBS. Symptoms of IBS occur in approximately 14% of otherwise apparently healthy people. IBS is a complex condition, in part because it is not a disease but a syndrome composed of a number of conditions with similar manifestations.

The compound anhydrous Form I 2-methyl-4-(4-methyl-1-piperazinyl)-10H-thieno-[2,3-b][1,5]benzodiazepine has antimuscarinic activity, 5-HT$_{2B}$ receptor activity, and is denoted for use in the treatment of certain gastrointestinal conditions. Thus, the compound is suggested for the treatment of Functional Bowel Disorders including, but not limited to, irritable bowel syndrome, gastric hypermotility, and related conditions.

When anhydrous Form I 2-methyl-4-(4-methyl-1-piperazinyl)-10H-thieno[2,3-b][1,5]benzodiazepine is used for the treatment of gastrointestinal disorders, it is more preferably used for the treatment of irritable bowel syndrome or gastric hypermotility disorder. When treating gastrointestinal disorders using anhydrous Form I 2-methyl-4-(4-methyl-1-piperazinyl)-10H-thieno-[2,3-b][1,5] benzodiazepine, it is most preferably used for the treatment of irritable bowel syndrome.

The anhydrous Form I 2-methyl-4-(4-methyl-1-piperazinyl)-10H-thieno-[2,3-b][1,5]benzodiazepine compound is effective over a wide dosage range, the actual dose administered being dependent on the condition being treated. For example, in the treatment of adult humans, dosages of from 0.25 to 30 mg, preferably from 1 to 20 mg, per day may be used. A once a day dosage is normally sufficient, although divided doses may be administered. For treatment of central nervous system disorders, a dose range of from 1 to 30 mg, preferably 2.5 to 20 mg per day is suitable. Radiolabelled anhydrous Form I 2-methyl-4-(4-methyl-1-piperazinyl)-10H-thieno-[2,3b][1,5] benzodiazepine, can be detected in the saliva and thus the compound can potentially be monitored in patients to assess compliance.

The anhydrous Form I 2-methyl-4-(4-methyl-1-piperazinyl)-10H-thieno-[2,3-b][1,5]benzodiazepine compound will normally be administered orally or by injection and, for this purpose, it is usually employed in the form of a pharmaceutical composition.

Accordingly, pharmaceutical compositions comprising anhydrous Form I 2-methyl-4-(4-methyl-1-piperazinyl)-

10H-thieno[2,3-b][1,5]benzodiazepine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 30 mg, more usually 1 to 30 mg, of the active ingredient. When a sustained release formulation is desired, the unit dosage form may contain from 0.25 to 200 mg of the active ingredient. A preferred formulation of the invention is a capsule or tablet comprising 0.25 to 30 mg or 1 to 30 mg of active ingredient together with a pharmaceutically acceptable carrier therefor. A further preferred formulation is an injection which in unit dosage form comprises 0.25 to 30 mg or 1 to 30 mg of active ingredient together with a pharmaceutically acceptable diluent therefor.

The formation of solvates is known to be an individualistic effect. The ability of a given compound to form a solvate is not predictable, to Applicant's knowledge. Further, the beneficial utility of such solvates is particularly surprising. The present invention provides a crystalline methylene chloride solvates of 2-methyl-4-(4-methyl-1-piperazinyl)-10H-thieno[2,3-b][1,5]benzodiazepine which have been verified using x-ray crystal techniques. This solvate is useful for providing pharmaceutically elegant Form I olanzapine. The solvates of this invention may be prepared by suspending 2-methyl-4-(4-methyl-1-piperazinyl)-10H-thieno[2,3-b][1,5]benzodiazepine in warm solvent or solvent mixture. Most preferably the solvent temperature is from about 0° C. to 100° C., although other reaction temperatures can be effective with alteration of the reaction conditions using known techniques. Another preferred solvent temperature range is from about 25° C. to about 80° C. It is further preferred when the temperature range is from about 25° C. to about 50° C. The mixture is most desirably stirred for about 30 minutes or more. The reaction time will vary with the temperature of the reaction, pressure, and with the completion of reaction desired.

The methylene chloride solvate may be isolated by cooling the mixture to ambient temperature or through the use of an antisolvent. The solvate is typically dried or azeotroped under ambient conditions; however, other common drying methods can be utilized if they are carefully controlled.

Further, the solvate of this invention is useful for preparing anhydrous Form I 2-methyl-4-(4-methyl-1-piperazinyl)-10H-thieno[2,3-b][1,5]benzodiazepine. Applicants have discovered that anhydrous Form I olanzapine can be prepared by drying or azeotroping the methylene chloride solvate and recrystallizing the material in an appropriate solvent in the presence of a Form I seed crystal to provide the desired Form I olanzapine. Such solvents are preferedly, one or more selected from the group consisting of aromatic solvents, $C_1$–$C_3$ alkyl acetates, and $C_1$–$C_3$ alkyl esters. Most preferred solvents are ethyl acetate, tetrahydrofuran, and toluene. A particularly preferred solvent is one containing ethyl acetate.

Surprisingly, the aforementioned process provides a pharmaceutically elegant Form I product having pharmaceutically acceptable color, potency $\geq$97%, total related substances <0.5% and an isolated yield of >73%.

The starting materials for the present invention can be prepared by a variety of procedures well known to those of ordinary skill in the art. The material to be employed as starting materials in the process of this invention can be prepared by the general procedure taught by Chakrabarti in U.S. Pat. No 5,229,382, ('382) herein incorporated by reference in its entirety.

The olanzapine crude product provided by the methods of the '382 patent typically exhibit a color which is undesired for commercial pharmaceutical use. Carbon treatment of the olanzapine crude product prepared using the '382 methods typically does not remove all of the undesired color. Therefore, greater purity was desired.

As used herein mixing steps may be accomplished using common agitation methods such as stirring, shaking, and the like. As used herein the phrase "producing crystalline product from the mixture" shall refer to crystallization from the stated mixture of compound and solvent. Further, the artisan recognizes that crystallization processes may include seeding, chilling, scratching the glass of the reaction vessel, and other such common techniques.

The concentration of reactants is not critical for the invention. The art worker can alter the concentration of the reactants to achieve the desired rate of reaction and product yield.

The length of time for carrying out the processes described will vary. As is always the case in chemistry, the rate of the reaction depends on a variety of factors, such as the temperature and the exact compound which is to be prepared. The course of the reaction may be followed using methods familiar to the skilled artisan.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

EXAMPLE 1

Methylene Chloride Solvate

A 5.0 g sample of technical grade 2-methyl-4-(4-methyl-1-piperazinyl)-10H-thieno[2,3-b][1,5]benzodiazepine was suspended in methylene chloride (40 g). The stirred mixture was heated to about 30° C. and maintained at about 30° C. for about 30 minutes. The mixture was chilled to about 5° C. using an ice bath. The resulting product was isolated using vacuum filtration.

We claim:

1. A mono(methylene chloride) solvate of a compound of formula I

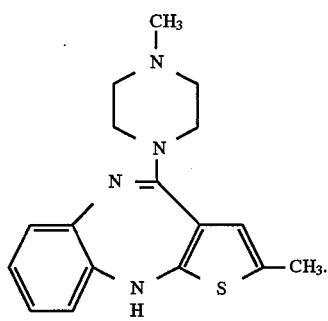 (I)
2. A solvate of claim 1 which is crystalline and has a typical X-ray powder diffraction pattern substantially as follows, using an Enraf-Nonius CAD4 kappa axis diffractometer, wherein d represents the interplanar spacing in Angstroms:
| d |
|---|
| 10.3721 |
| 9.4579 |
| 8.0541 |
| 7.4887 |
| 6.7033 |
| 6.5341 |
| 5.6880 |
| 5.5067 |
| 5.2097 |
| 4.7905 |
| 4.5342 |
| 4.3932 |
| 4.1624 |
| 4.0157 |
| 3.9705 |
| 3.8522 |
| 3.7535 |
| 3.6804 |
| 3.6335 |
| 3.5198 |
| 3.489 |
| 3.4399 |
| 3.3491 |
| 3.2431 |
| 3.1714 |
| 3.1075 |
| 3.0437 |
| 2.9476 |
| 2.8872 |
| 2.8466 |
| 2.7906 |
| 2.7239 |
| 2.6859 |
| 2.6116 |
| 2.5729. |
* * * * *